United States Patent [19]

Gray, Jr. et al.

[11] Patent Number: 4,476,345
[45] Date of Patent: Oct. 9, 1984

[54] N-PARAFFIN-ISOPARAFFIN SEPARATION PROCESS USING WASH OF RECYCLE PURGE GAS

[75] Inventors: Robert L. Gray, Jr., Mahopac; Thomas C. Holcombe, Scarsdale, both of N.Y.

[73] Assignee: Union Carbide Corporation, Danbury, Conn.

[21] Appl. No.: 434,398

[22] Filed: Oct. 14, 1982

[51] Int. Cl.³ .................. C10G 25/00; C10C 7/12
[52] U.S. Cl. .................. 585/820; 208/310 Z
[58] Field of Search .................. 208/310 Z; 585/820, 585/822, 825

[56] References Cited

U.S. PATENT DOCUMENTS

| | | |
|---|---|---|
| 3,258,417 | 6/1966 | Hess et al. .................. 208/310 Z |
| 3,309,415 | 3/1967 | Young et al. .................. 208/310 Z |
| 3,422,005 | 1/1969 | Avery .................. 208/310 Z |
| 3,700,589 | 10/1972 | Symoniak et al. .................. 208/310 Z |
| 3,726,792 | 4/1973 | Francis et al. .................. 208/310 Z |
| 3,753,896 | 8/1973 | Brian et al. .................. 208/310 Z |
| 3,770,621 | 11/1973 | Collins et al. .................. 585/825 X |
| 4,176,053 | 11/1979 | Holcombe .................. 585/822 X |
| 4,210,771 | 7/1980 | Holcombe .................. 585/701 |
| 4,354,929 | 10/1982 | Wessels et al. .................. 208/310 Z |
| 4,374,022 | 2/1983 | Fuderer .................. 208/310 Z |

Primary Examiner—Delbert E. Gantz
Assistant Examiner—Glenn A. Caldarola
Attorney, Agent, or Firm—Frederick J. McCarthy, Jr.

[57] ABSTRACT

An invention is described in which a portion of one of the product streams from an adsorption system is used to wash a recycle gas stream in order to improve the quality of one of the products.

1 Claim, 6 Drawing Figures

N-PARAFFIN-ISOPARAFFIN SEPARATION PROCESS USING WASH OF RECYCLE PURGE GAS

The present invention relates in general to the separation of mixtures of normal and non-normal paraffins. More particularly the present invention relates to lowering the amount of undesired residuals in the recycle purge gas utilized in such separation.

The separation of mixtures of chemical compounds into two or more fractions by selective adsorption based on molecular size is a conventional procedure which takes advantage of the uniform diameters of pores of a given zeolitic molecular sieve adsorbent. The separation of normal paraffins from isoparaffins has been found to be particularly adapted to this technique and a number of processes have been proposed for this purpose. Most of them have been based on contacting the mixed hydrocarbon feed in the vapor phase with a 5 Angstrom molecular sieve to adsorb the straight chain hydrocarbon compounds followed by desorption of the straight chain compounds at a lower pressure or higher temperature usually with the aid of a purge gas. Some have been done with little or no change in temperature of pressure by employing a purge which is sufficiently strongly adsorbed to exert a displacing action on the adsorbed straight chain compounds. One process of particular interest operates under essentially isobaric and isothermal conditions even though desorption is accomplished using a non-sorbable purge gas instead of a strongly sorbable purge material. That process is defined in detail in U.S. Pat. No. 3,700,589, issued Oct. 24, 1972, the disclosure of which is incorporated herein by reference. An improvement of the aforesaid patent is described in U.S. Pat. No. 4,176,053 issued Nov. 27, 1979 the disclosure of which is also included herein by reference.

The present invention is an improvement of the foregoing processes which enables the lowering of the undesired residuals in recycled purge gas utilized in said processes. Also the present invention is similarly an improvement in the TIP process referenced to and disclosed in U.S. Pat. No. 4,210,771 issued July 1, 1980.

In accordance with a particular embodiment of a process, at which the present invention is an improvement, for separating normal paraffins from a mixture with non-normal paraffins; e.g. the process of U.S. Pat. No. 4,176,053, a feedstock mixture of same in the vapor state and at superatmospheric pressure is passed periodically in sequence through each of at least four fixed beds of a system containing a zeolitic molecular sieve adsorbent having effective pore diameters of substantially 5 Angstroms, each of said beds cyclically undergoing the states of:

(a) adsorption-fill, wherein the vapor in the bed void space consists principally of a non-sorbable purge gas and the incoming feedstock forces the said non-sorbable purge gas from the bed void space out of the bed without substantial intermixing thereof with non-adsorbed feedstock fraction;

(b) adsorption, wherein the feedstock is cocurrently passed through said bed and the normal constituents of the feedstock are selectively adsorbed in the internal cavities of the crystalline zeolitic adsorbent and the nonadsorbed constituents of the feedstock are removed from the bed as an effluent having a greatly reduced content of normal constituents;

(c) void space purging, wherein the bed loaded with normals adsorbate to the extent that the stoichiometric point of the mass transfer zone thereof has passed between 85 and 97 percent of the length of the bed and containing in the bed void space a mixture of normals and non-normals in essentially feedstock proportions, is purged countercurrently, with respect to the direction of adsorption stage (b), by passing through the bed a stream of non-sorbable purge gas in sufficient quantity to remove said void space feedstock vapors but not more than that which produces about 50 mole percent, preferably not more than 40 mole percent, of absorbed feedstock normals in the bed effluent; and (d) purge desorption, wherein the selectivity adsorbed feedstock normals are recovered as a product stream by passing a non-sorbable purge gas countercurrently with respect to adsorption stage (b) through the bed until the major proportion of adsorbed normals has been desorbed and the bed void space vapors consist principally of non-sorbable purge gas.

The above-noted process further comprises the recycling directly in the vapor phase, in combination with feedstock, the mixture of normals and non-normals purged from each bed of the system during stage (c) to another bed of the system undergoing stage (b) adsorption.

In conventional practice the effluents from the bed during void space purging, stage (c), have been cooled to condense the higher boiling paraffin constituents, flashed to remove and recover any non-sorbable purge gas content.

The molecular sieve adsorbent employed in the above-noted process and the present invention can be any of the naturally occurring or synthetically produced three-dimensional crystalline zeolitic aluminosilicates from which the water of hydration can be removed without collapse of the crystal lattice and which will selectively, on the basis of molecular size, adsorb normal paraffins from the mixture thereof with branched chain and/or cyclic paraffins which comprises the feed stream. Since normal paraffins have a nominal cross-sectional diameter of about 5 Angstroms, molecular sieves having pore diameters of about 5 Angstroms are preferred for the practice of the present invention. Especially suitable are the cation forms of zeolite A which have a pore diameters of about 5 Angstroms. Zeolite A is well known in the art as a synthesized zeolite having a very large adsorption capacity and, depending on the cation species present, exhibit apparent pore diameters ranging from about 3 to about 5 Angstroms. As prepared in the sodium cation form, zeolite A has pore diameters of about 4 Angstroms. When 25 percent, preferably at least 40 percent, of sodium cations are exchanged by calcium and/or magnesium cations, the effective pore diameter increases to about 5 Angstroms. Zeolite A as used herein in the Specification and claims is intended to the denote the zeolite described and defined in U.S. Pat. No. 2,882,243. Other zeolite molecular sieves which, in appropriate cation forms have pore diameters of about 5 Angstroms and which, although having less adsorption capacity than zeolite A, are suitably employed include zeolite T, U.S. Pat. No. 2,950,952 and the minerals chabazite and erionite.

The hydrocarbon streams treated in accordance with the present invention consist essentially of mixture of branched chain paraffins and normal paraffins boiling in the gasoline and kerosene ranges. Such mixtures occur as petroleum naphthas, both light and heavy, natural gasolines and natural gas condensates, but can be the products of processed outside the petroleum production and refining industry. In general, the hydrocarbons of these streams contain from about 4 to about 13 carbon atoms and preferably are substantially free of olefinically and acetylenically unsaturated species. It is also advantageous that sulfur compound impurities, if present, be present in a concentration less than about 400 parts per million, and the water impurity levels are below staturation. Although the process is operable regardless of the relative molar proportions of normals and non-normals present in the feed, the greatest benefit is afforded when the process is operated as one of bulk separation wherein both non-normals and normal paraffins each constitute at least 10 mole percent of the feedstock.

The entire process is operated at a substantially uniform temperature selected from the range of about 350° F. to 750° F. At temperatures below about 350° F., the efficiency of the non-sorbable purge gas is decreased to the point where undesirably large quantities are required adequately to purge the normals from the bed. Above about 750° F., the rate of coke deposition increases rapidly and the need for more frequent oxidation regenerations of the adsorbent arises. It is to be understood that the denomination of the process as being "isothermal" is done so for the reason that the temperature of the feed and purge gas stream are essentially the same, i.e., within about 30° F., when entering the bed. In this, as in any adsorption-desorption cycle, it is possible for thermal gradients to develop in the bed due to heats of adsorption and desorption.

The pressure range suitable for the present process is from about 50 psia to about 400 psia. In general, the preferred pressure is dependent on the particular feedstock involved, with the higher pressures being used for the more volatile feedstocks to enhance the separation obtained and to facilitate the condensation of the product effluents. It is important that none of the feedstock components condense in the void space of the bed since such liquid phase material cannot be removed by the limited quantity of nonsorbable purge gas allotted for this purpose.

Accordingly, the pressure is to be maintained at less than 80 percent of the critical pressure of the highest boiling key component of the feed or less than about 60 percent of the dew point pressure of the feed at the process temperature, whichever is the lower value. Similarly, as in the case of the term "isothermal" supra, the process is termed "isobaric" because the pressure of the adsorber feed and purge gas streams are within conventional limits the same at their respective influent ends of the bed. The term "isobaric" is thus used in its accepted sense in the art to indicate that the present process does not utilize a pressure swing type of desorption. By the term "key component" used herein in conjunction with the delineation of pressure requirements is meant any paraffinic constituent of the feed mixture which is present in significant amount. As is well understood in the art, what constitutes a significant quantity of a particular component of a mixture depends somewhat on the other components present and the nature of the treatment the feed is undergoing. Generally, however in the present process, a key component will be present in an amount of about 10 mole percent or greater.

When the pressure conditions are dictated by the dew point criterion, the dew point of the hydrocarbon mixture involved can be determined by the procedure set forth in "Process Heat Transfer," Kern, Donald Q., McGraw-Hill Book Company, New York, N.Y. (U.S.A.), at pages 319 to 325 inclusive. Other procedures are well known in the art to make these calculations. Routine experimentation can, of course, be resorted to, instead of calculating the dew point.

The non-sorbable purge gas used to flush the bed void space vapors and carry from the bed desorbed normal paraffins in this process is any permanent gas or mixture of such gases which have molecular dimensions sufficiently small to enter the intracrystalline cavities of the molecular sieve, but are not themselves strongly enough adsorbed to displace the normal hydrocarbons adsorbed thereon to any significant degree. Nitrogen, hydrogen, helium and methane are such materials and are preferred in the practice of this invention. Other permanent gases are known in the art, but lack of commercial availability at reasonable cost renders them impractical although operable.

Bed void space for purposes of this invention is intended to mean any space in the bed not occupied by solid material except the intracrystalline cavities of the zeolite crystals. The pores within any binder material which may be used to form agglomerates of the zeolite crystals is considered to be bed void space.

As stated hereinbefore, the adsorption stroke wherein the normal paraffins are selectivity adsorbed on the bed is continued for a period such that the stoichiometric point of the normal hydrocarbons mass transfer zone has moved through between 85 and 97 percent of the bed length. The term mass transfer zone as used herein has the same meaning as is generally accepted in the art, i.e., it denotes that section of the adsorbent bed in which the adsorbate loading of the adsorbent bed and the concentration of the adsorbate fraction in the fluid stream are both increasing with time. The "stoichiometric point" lies within the mass transfer zone and is that point at which the expended capacity of the leading section of the mass transfer zone is equal to the unexpended capacity of the transfer zone.

In order to optimize the four stage cycle of the process and to give a substantially constant flow of both normal and non-normal hydrocarbon product streams, it is preferred to use at least four adsorption beds of essentially equal capacity in an integrated time-controlled sequence. This system provides optimum conditions for heat exchange and purge gas recovery, as well as favorable mass transfer and pressure drop characteristics during the adsorption stage (b). All process valves can be automatically controlled from a timer control system. For purposes of illustrating the exemplary flows for the cycling of adsorbers with a feedstock as set forth in Table I, the following description is provided in conjunction with FIG. 1 of the drawing which is a flow diagram of such a four stage cycle process using a seven bed adsorbent system. This description is applicable to the naptha range, n-paraffin/isoparaffin separation process of the present invention regardless of the quantity or composition of the mixed pentanes/hexanes feedstocks used in the present invention, examples of which are provided hereinbelow. For purposes of the exemplification, it is presumed that the system has already attained a steady state. The temperature of all primary adsorption beds and all feed streams to and effluents therefrom is 700° F. The beds are under a pressure of about 250 psia. The composition of the primary feedstock is shown in tabular form below:

TABLE I

| Saturated Hydrocarbon | Non-normals, wt % of Component in Feed | Wt % Normals in Feedstock |
| --- | --- | --- |
| $C_3$ | | Trace |
| $C_4$ | 0.60 | 1.60 |
| $C_5$ | 33.37 | 12.52 |
| $C_6$ | 44.66 | 5.92 |
| $C_7$ | 1.33 | Trace |
| $C_8+$ | Trace | Trace |

Figure 1:
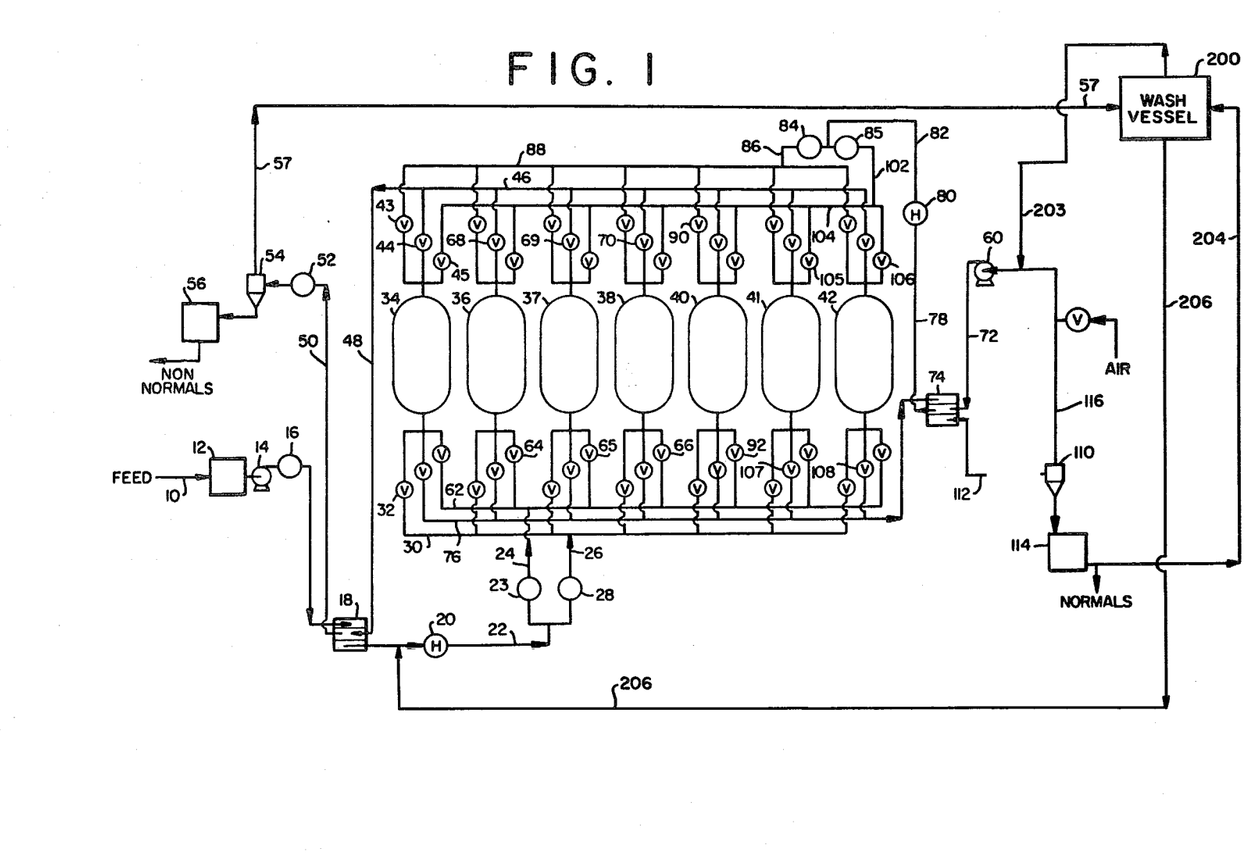

With reference to FIG. 1 of the drawing, the feed stream is fed through line 10 to accumulator tank 12 from which it is drawn by pump 14 through a feed rate controller 6 and thereafter heat exchanger 18 where it is heated to about 450°–500° F. by heat exchange with effluent from an adsorption bed undergoing second stage adsorption. The partially heated feed stream is raised to full 700° F. operating conditions in a gas fired heater 20. The flow rate of the feed stream from heater 20 into line 22 is 356,578 pounds per hour and has a normal paraffin content of about 20.0 wt %. The stream from line 22 is directed partially to line 24 by way of pressure controller 23 (the use of which will be described later) and partially to line 26 by means of flow rate controller 28 in line 26. Through line 26 the minor portion of the feed from line 22, namely 99,026 pounds per hours, is directed through manifold 30 and valve 32 to adsorption bed 34. Each of the seven adsorption beds in the system, namely beds 34, 36, 37, 38, 40, 41 and 42 contain 93,000 pounds of calcium zeolite A in the form of 1/16 inch cylindrical pellets. Each bed is 17.5 feet long and 12.5 feet in diameter. Bed 34, at the time that feed passing through valve 32 enters, contains residual hydrogen purge gas from the preceding desorption stroke. The rate of flow of the feed through line 26, manifold 30 and valve 32 is controlled such that bed 34 is flushed of residual hydrogen uniformly over a period of about one minute i.e., the effluent from bed 34 exists at a rate of about 3,845 pounds per hour. During this first stage of the adsorption stroke in bed 34, the hydrogen effluent passes from the bed through valve 45 into manifold 104. During the one minute period when the hydrogen was being flushed from bed 34, feed passes from valve 23 through line 24, through manifold 62, and valves 64, 65 and 66 to beds 36, 37 and 38 respectively at the rate of 79,184 pounds per hour. The normal paraffins in the feed are adsorbed by each of beds 36, 37, 38 and the non-adsorbed non-normal and residual hydrogen purge gas emerge from the beds through valves 68, 69, 70 respectively and fed to manifold 46. The non-normals and residual hydrogen purge gas flow through line 48, heat exchanger 18, line 50, water cooler 52, separator 54 an the condensed product is accumulated in accumulator 56. The residual hydrogen purge gas in the non-normals effluent leaves separator 54 through line 57 and ultimately to purge recycle compressor 60 via line 203.

Since the recycle purge gas separated form the non-normals effluent inevitably contains at least a small amount of non-normals, the direct introduction of the recycle purge gas to recycle compressor 60 would result, in the course of second stage desorption, in non-normals passing through with desorbed normals in manifold 76 to normal product accumulator 114, thus detrimentally affecting the purity of the normals product.

In accordance with the present invention the recycle purge gas in line 57 containing residual non-normals is introduced to a wash vessel 200, which can be a trayed or packed column, wherein the recycle purge gas is washed with a small portion of the normal product introduced into the wash vessel 200 via line 204. In the wash vessel 200 the residual non-normals in the recycle purge gas are essentially displaced by normals product and recycle purge gas with lowered non-normal content is returned to recycle compressor 60 via line 203. The stream exiting wash vessel 200 via line 206 contains "wash" normals and non-normals removed from the recycle purge gas and this stream is re-cycled to the feed.

During the one minute period when the residual hydrogen is being flushed from bed 34, i.e. stage (a), bed 40 is undergoing the first stage of purging with hydrogen wherein the hydrocarbons in the bed void space are being flushed from the bed, i.e., stage (c). During the same one minute interval, beds 41 and 42 are undergoing the second stage of desorption, i.e., stage (d), in which the normal hydrocarbons are desorbed from the molecular sieve adsorbent using hydrogen and removed from the bed. From compressor 60, the hydrogen gas stream is passed through line 72 and through heat exchanger 74 wherein it is heated to about 550°–600° F. by heat from hot desorbed normals from any of the adsorption beds flowing through manifold 76. From the heat exchanger 74 the hydrogen gas stream passes through line 78 to gas fired heater 80 where it is heated to 700° F. and hence through line 82. By means of flow controllers 84 and 85 the gas flow from line 82 is divided into two streams, the lesser stream being passed at the rate of 7,709 pounds per hour through line 86, manifold 88, and valve 90 countercurrently (with respect to the previous adsorption stroke) through bed 40. The low controlled flow rate employed for the one minute first stage desorption is for the purpose of flushing non-adsorbed hydrocarbon from the bed voids without causing excessive desorption of the normals from the adsorbent. The effluent from bed 40, consisting of 124,693 pounds per hour hydrocarbon and 2,038 pounds per hour hydrogen passes through valve 92 and into manifold 62. The effluent from the first stage of desorption containing the void space loading from the previous adsorption stroke plus any desorbed normals is recycled directly to the feed used during the second stage of adsorption without intermediate cooling, phase separation and reheating. In fact, valve 92 is used as the second stage adsorption feed valve when bed 40 is on that step in the cycle. The major portion of the hydrogen stream from line 82, namely 37,659 pounds per hour is passed through control valve 85, line 102, to manifold 104 where it is mixed with the previously mentioned first stage adsorption effluent from valve 45 and thence equally through valves 105 and 106 through beds 41 and 42. During this period, selectively adsorbed normal paraffins are desorbed from the zeolitic molecular sieve and flushed from the bed. The effluent from beds 41 and 42 consisting of 85,000 pounds per hour normal paraffins and 20,654 pounds per hour hydrogen are fed through valves 107 and 108 to manifold 76 and thereafter through heat exchanger 74. The cooled normal paraffins and hydrogen leaving heat exchanger 74 are fed to separator 110 through line 112 wherein the normals are fed to normals accumulator 114 and the hydrogen recycled to purge recycle compressor 60 through line 116.

The foregoing description is for a single one minute period of seven minute cycle of the system. For the next one minute period, appropriate valves are operated so that bed 34 begins a second stage adsorption stroke beds 37 and 38 remain on second stage adsorption, bed 36 begins a first stage desorption, bed 40 enters a second stage desorption, bed 41 remains on desorption and bed 42 begins a first stage adsorption stroke. Similarly a new cycle begins after each one minute period and at the end of a seven minute period, the beds have all gone through all stages of adsorption and desorption. The following charts indicate the functioning of each of the seven beds for each one minute period. In the chart, A-1 denotes the stage (a) adsorption in which a bed is flushed of residual hydrogen using a feedstock stream at low feed rates. A-2 denotes a conventional adsorption stroke, i.e., the stage (b) adsorption herein, in which the rate of feed of the hydrocarbon mixture is commensurate with efficient use of the bed. D-1 denotes the stage (c) desorption in which purge gas is used in an amount sufficient to remove hydrocarbon vapor from the bed void spaces, and D-2 denotes stage (d), i.e., hydrogen purge using flow rates sufficient to desorb normals from the bed.

| Time, min | TIME SEQUENCE | | | | | | |
|---|---|---|---|---|---|---|---|
| | 0 | 1 | 2 | 3 | 4 | 5 | 6 |
| Bed 34 | A-1 | A-2 | A-2 | A-2 | D-1 | D-2 | D-2 |
| Bed 36 | A-2 | D-1 | D-2 | D-2 | A-1 | A-2 | A-2 |
| Bed 37 | A-2 | A-2 | D-1 | D-2 | D-2 | A-1 | A-2 |
| Bed 38 | A-2 | A-2 | A-2 | D-1 | D-2 | D-2 | A-1 |
| Bed 40 | D-1 | D-2 | D-2 | A-1 | A-2 | A-2 | A-2 |
| Bed 41 | D-2 | D-2 | A-1 | A-2 | A-2 | A-2 | D-1 |
| Bed 42 | D-2 | A-1 | A-2 | A-2 | A-2 | D-1 | D-2 |

The purpose of the valve 23 in the A-1 feed line 24 is best shown by the following example. Assume a feed pressure in line 22 of 250 psia and also assume for purposes of this example that flow control valves 28, 84 and 85 and all line have negligible pressure drop. Then A-1 feed lines 26 and 30 are at 250 psia. A-1 effluent line 104 reflecting the pressure drop through the adsorber vessel is a 249 psia. This then must be the pressure of lines 102, 82, 86 and the D-1 feed line 88. The D-1 effluent line 62 reflecting the pressure drop through the adsorber vessel is at 246 psia. Since line 62 and line 24 are also the A-2 feed lines, their pressure is about 246 psia. In this example, therefore, line 24 must be controlled by value 23 to 4 psi lower than line 22 to ensure the mixing of D-1 effluent and the A-2 feed.

As a bed is cycled at the 700° F. operating temperature, a carbonaceous deposit gradually accumulates. This deposit reduces the capacity of the adsorbent, which results in a breakthrough of normal paraffins into the isomer product stream and decreased normal paraffin recovery. The rate at which this deposit accumulates depends on factors such as temperature, feed impurities, feed properties, cycle time, and residual paraffin loadings. This type of adsorbent deactivation is temporary as that original bed capacity can be restored by burning off this deposit under controlled conditions.

Oxidative regeneration is a blocked operation with burnoff of the five adsorbent beds in sequence, and is required to maintain the working capacity of the molecular sieve. The basis for this procedure is a three-day shutdown consisting of the following stages:

| Stage: | Time, hrs. |
|---|---|
| (1) System preparation for regeneration | 2 |
| (2) Oxidative regeneration | 68 |
| (3) System preparation for adsorption step | 2 |
| Total time | 72 |

When the beds have been cycled to the point that oxidative regeneration is required, the normal process cycle is shut down, and the beds undergo an additional long desorption purge to remove as much of the residual normal paraffins as possible. Countercurrent circulation of nitrogen is established by means of the purge gas compressor 60 at 100 psia and 750° F. The circulation of the hot nitrogen has two purposes, namely to sweep the purge gas from the bed if it is combustible (i.e., fuel gas, hydrogen, etc.), and to raise the temperature of the bed to above the coke ignition point prior to introduction of oxygen into the system. The effluent gas from the beds manifold 76 is cooled to condense the hydrocarbons and water that are desorbed. When the bed is up to temperature, air is introduced into the circulating stream at a rate such that the oxygen content of the gas entering the bed is between 0 and 1 percent by volume. The oxygen in the gas combusts with coke in the top of the bed. The heat released from combustion is carried out of the burning zone as a preheat front traveling ahead of the burning front. This preheat front raises the bed temperature to about 950° F. This temperature is controlled by regulating the amount of oxygen in the entering gas. Internal pellet temperatures in excess of 1300° F. will permanently destroy the molecular sieve crystal so the gas phase temperature is held to a maximum of 1000° F. As the burning front passes through the bed, the temperature will drop back to the gas inlet temperature of 750° F. Since the coke deposit contains hydrogen, water is formed during combustion in addition to carbon oxides. This water must be removed from the system because the molecular sieve is permanently damaged by repeated exposure to water at high temperatures. A refrigeration unit is used to remove most of the water, thereby minimizing this damage.

Figure 2:
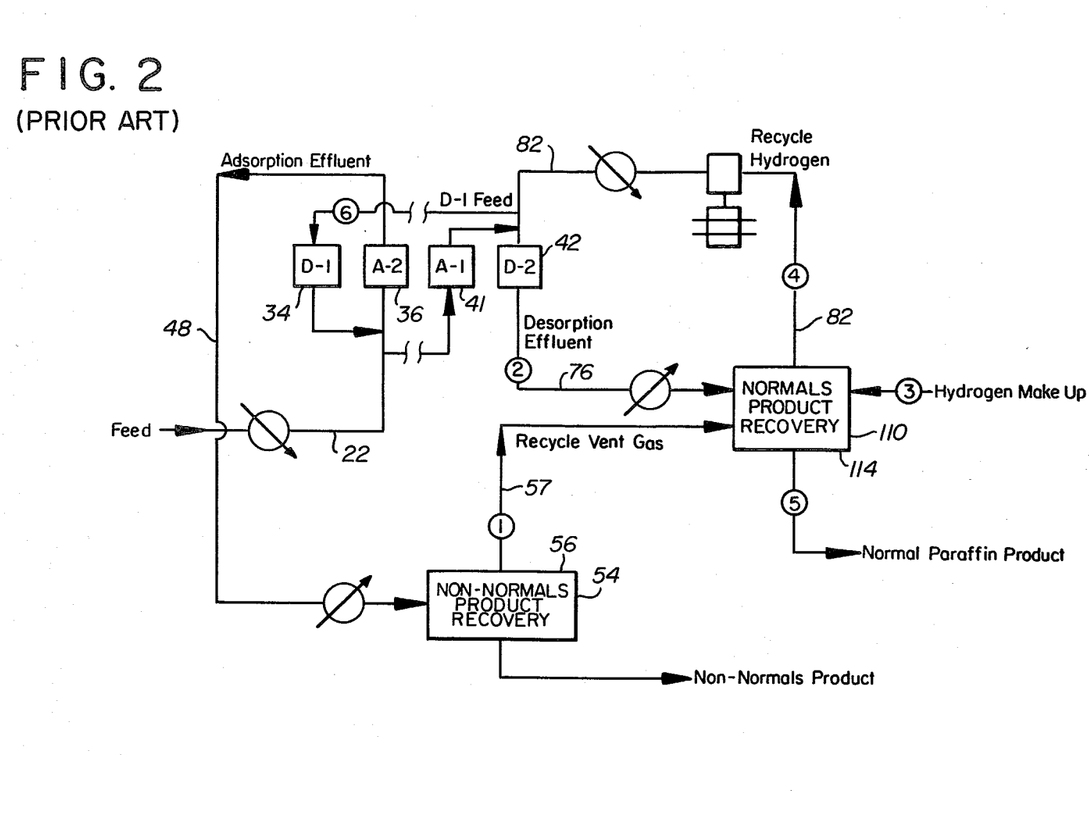

FIG. 2 depicts a simplified prior art flow scheme designed to treat a primarily hexane feedstock and produce a high purity normal hexane product using conventional technology of cooling the streams to recover the products from the recycle gas instead of the "wash" of the present invention. Table A shows a material balance around the normal product recovery section of the unit.

In the conventional prior art unit with reference to FIG. 2, normals product purity is controlled in two ways. First a level of cooling is maintained on the recycle vent gas (Str. 1, FIG. 2), in order to minimize its concentration of non-normal hydrocarbon before the stream enters the normal product recovery section. The second way is to counter-currently purge an adsorber, which has just completed an adsorption step, with hydrogen (D-1 step, Str. 6, FIG. 2), to remove feed non-normals from the void space inside the vessel. Non-normals which remain in the void space after this step will enter the normal product during the desorption step. It should be noted that any hydrogen which leaves the bottom of an adsorber during the D-1 step, will enter an adsorber on a hydrocarbon feed step (A-2) and will ultimately end up as recycle vent gas (Str. 1, FIG. 2).

The material balance in Table A shows a $C_5+$ normal hexane product purity of 96.3 mole percent for the conventional unit of FIG. 2. Of the 2.00 moles/hr of non-normals in the normal product, it can be calculated from the material balance that 1.41 moles per hr. (47%) of these come from the void spaces at the end of the D-1 step, 1.56 moles/hr (52%) come from the recycle vent gas and 0.02 moles per hour (1%) comes from the hydrogen make up.

Increasing the normal product purity beyond the 96.3 mole percent with the prior art flow scheme in FIG. 2 is costly and impractical. Lowering the temperature in the product recovery sections is expensive from the investment, utilities and maintainence standpoint and would require feed drying as a pre-treatment step. Increasing the hydrogen feed during the D-1 purge step will not work. Most of the non-normals are removed from the vessel near the beginning of the D-1 step and as the step continues, decreasing amounts of non-normals are removed. As this D-1 purge rate is increased, more purge gas leaves the bottom of a vessel on the D-1 step and ultimately carries non-normals into the normal product recovery section via the recycle vent gas. When the quantity of non-normals removed per mole of purge gas during the D-1 step becomes less that the quantity of non-normals carried back to the normal product recovery section by that same mole of gas, increasing the flow to the D-1 step will lower the normal product purity instead of increasing it. However, incorporating the normals product wash into the prior art unit flow scheme, in accordance wiht the present invention, can increase the normal product purity with only a small (2%) increase in adsorbent inventory and about a 5% increase in compressor horsepower.

Figure 3:
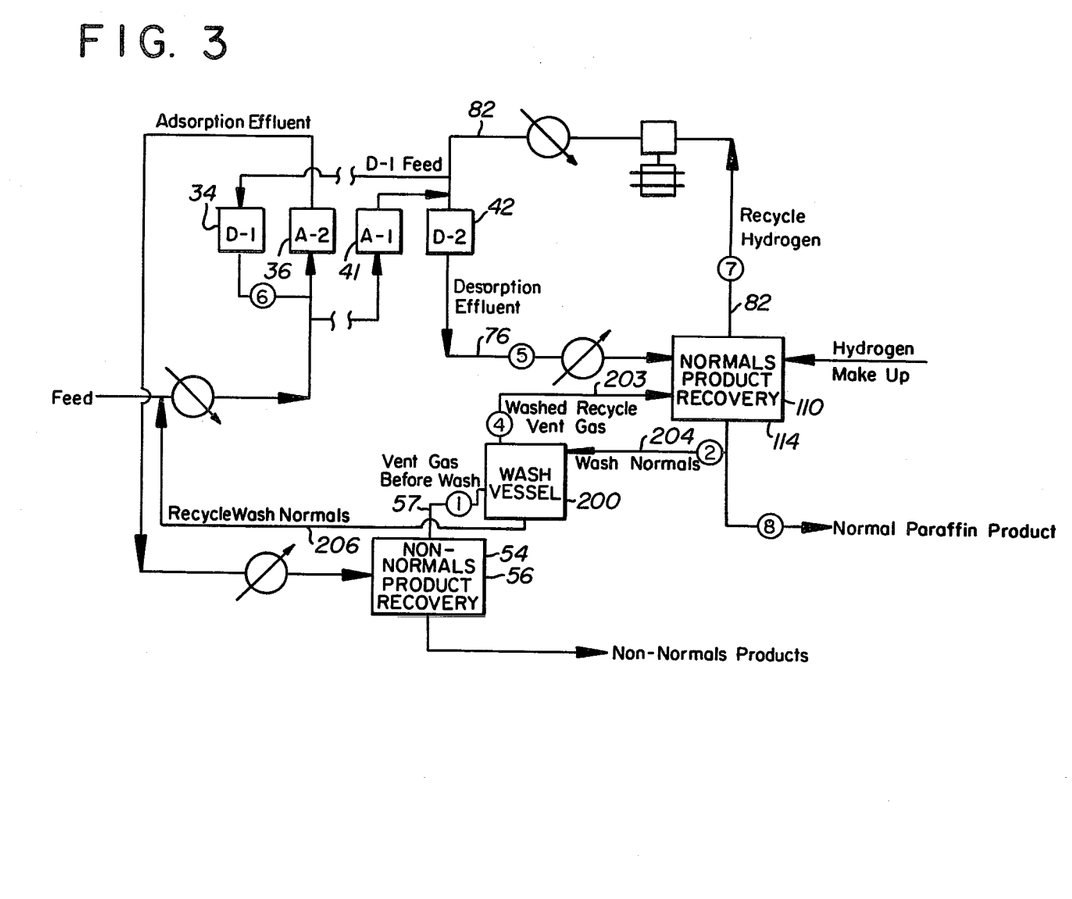

FIG. 3 shows the same prior art processing unit as in FIG. 2, with the addition of normals product washing in accordance with the present invention used to increase the $C_5+$ normal hexane product purity from 96.3 to 97.6 mole percent. In FIG. 3, in accordance with the present invention, the recycle vent gas is washed counter-currently with a small quantity about (5.5%) of the normals product in a trayed or packed column. The washed recycle vent gas leaving the top of the wash column carries considerably less non-normals back to normals product recovery section than in the prior art scheme (FIG. 2). The recycle wash normals (Str. 3, FIG. 3) flow back to the feed point carrying with it the recovered non-normals. The wash vessel in this arrangement was simulated with one theoretical stage. Increasing the number of theoretical stages to two or three will reduce the quantity of wash normals needed to obtain the same increase in product purity.

Table B shows a material balance for the normal product washing and normal product recovery section of FIG. 3 in accordance with the present invention. Of the 1.72 moles per hr. of non-normals in the $C_5+$ normals products (Str. 8, FIG. 3), it can be calculated from the material balance that 1.28 moles per hr. (74%) of these come from the void spaces at the end of a D-1 step, 0.42 mole per hr. (25%) comes from washed recycle vent gas and 0.02 mole per hr. (1%) comes from hydrogen makeup.

The above mentioned material balance information shows that the contribution of the recycle vent gas non-normals, to that of the total $C_5+$ impurities in the normals product, has been reduced to 27 percent of the quantity found in the product when not using normals product washing. An added advantage of the normals product wash is that the D-1 step feed rate can now be increased to a higher quantity without having a negative impact on the normals product purity.

In place of providing a higher normal product purity, the product wash embodiment of the present invention could also be used to reduce the investment and utilities of the unit for the same product purity (96.3 mole %). By reducing the recycle vent gas non-normals concentration, the quantity of non-normals left in the vessel at the end of a D-1 step can almost be doubled, thereby requiring less D-1 step purging. Lowering the D-1 purge rate reduces the quantity of normals recycled back to the adsorption feed point (Str. 6, FIG. 2) and therefore reduces the required adsorbent inventory. In this case, the reduction in adsorbent inventory would be around 10 percent.

The present invention is also applicable to what is known as the TIP process described in U.S. Pat. No. 4,210,771 which is a process for improving the octane rating of certain petroleum fractions by virtually complete isomerization of the normal paraffin hydrocarbons contained in a feed stream essentially of mixed normal and non-normal hydrocarbons, more particularly, to virtually complete isomerization of normal pentanes and normal hexanes contained in a feed stream containing normal pentanes and normal hexanes, as well as non-normal hydrocarbons to form branched chain iso/-pentanes and iso/hexanes.

Figure 4:
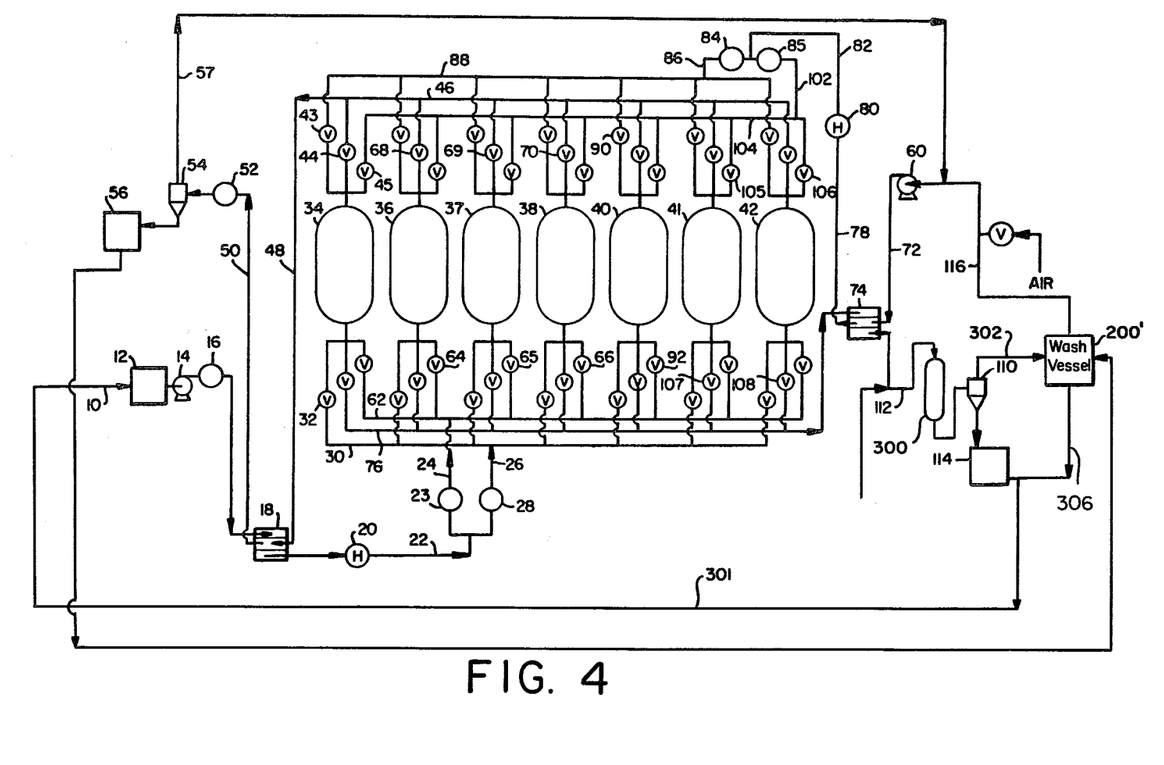

Essentially, the TIP process comprises passing a stream containing a mixture of normal and non-normal hydrocarbons into an isomerization reactor to catalytically isomerize at least a portion of the normals in the presence of hydrogen by contact in the reactor with a catalyst composition, which preferably is a zeolitic molecular sieve with a hydrogenation component. Other catalyst compositions such as alumina-base catalysts may be used as well. The temperature of the reactor is dependent in part on the particular catalyst employed, but preferably is within the range of 200° C. to 390° C. and the pressure in the reactor ranges between 175 psia and 600 psia when a molecular sieve catalyst is employed. The effluent from the reactor still contains approximately 20–30 wt-% normals. The hydrocarbon fraction of the reactor effluent stream is circulated to a zeolitic molecular sieve adsorbent bed where the normals are selectively adsorbed and the non-normals are passed out to the adsorber as an adsorber effluent and eventually an isomerate product. The normals are then desorbed from the bed using a hydrogen purge stream. FIG. 4 illustrates an arrangement for the practice of the TIP process which incorporates the "wash" of the present invention. With reference to FIG. 4 an isomerization reactor, such as described in U.S. Pat. No. 4,210,771, is provided at 300 and receives via line 112 normal paraffins and recycle hydrogen gas together with feed e.g. mixed pentanes and hexanes. The isomerized product and recycle gas, which in this case contains residual normals, are transferred to separator 110 from which the isomerization product is transferred via line 301 to the absorption bed for processing, as hereinabove described in connection with FIG. 1, with the product in this case being non-normals, which are recovered at 56. The recycle purge gas from separator 110 contains residual normals which, if not removed, decrease the purity of the non-normals product recovered at 56. Consequently, in accordance with the present invention, the recycle purge gas from separator 110 is fed via line 302 into wash vessel 200 e.g., a trayed or packed column, wherein the recycle purge gas is washed with a small portion of the non-normals product introduced into the wash vessel 200 via line 304. In the wash vessel 200 the residual normals in the recycle purge gas are essentially displaced by non-normal product and the recycle purge gas with lowered normal content is returned to recycle compressor 60 via line 303. The stream exiting wash vessel 200 via line 306 contains "wash" non-normals and normals removed from the recycle purge gas and this stream is recycled to the absorption bed with normals from accumulator 114.

Figure 5:
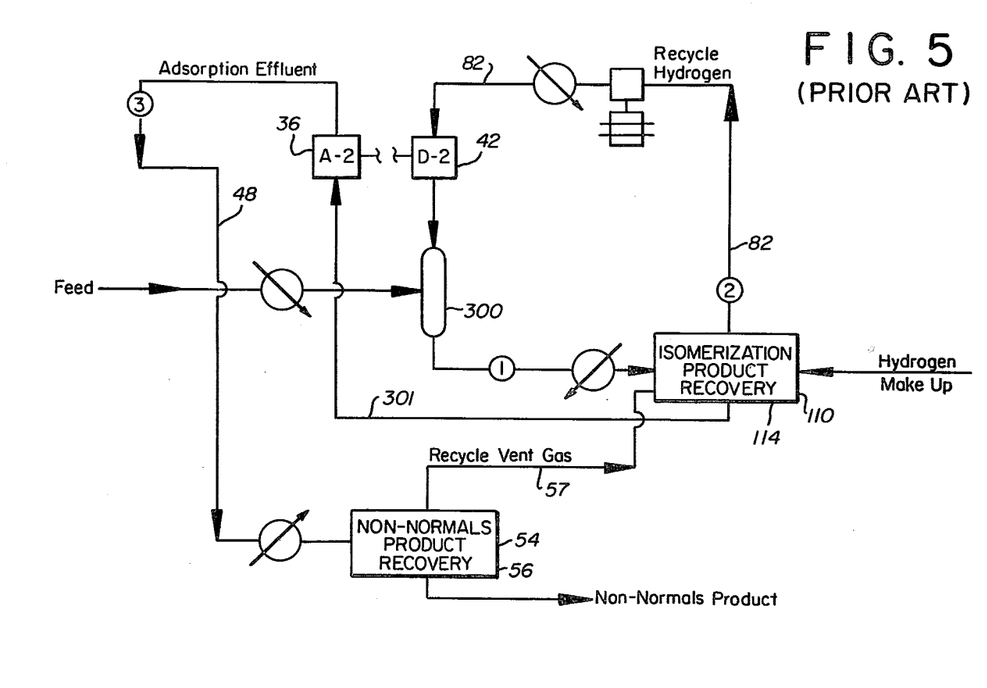

FIG. 5 depicts a simplified flow scheme of a prior art Total Isomerization Process (TIP) unit designed to treat a pentane/hexane feedstock and produce one high purity non-normal product which uses conventional cooling to recover hydrocarbons from the recycle hydrogen instead of the "wash" of the present invention. Normal paraffin in the recycle hydrogen in the TIP process contribute to inefficiencies and product impurities in the TIP process, in which the product is non-normal paraffins. Normal paraffin are adsorbed/desorbed from molecular sieve adsorbent due to a swing in their partial pressure over the adsorbent. A higher concentration of normal paraffin in the recycle hydrogen (Str. 2, FIG. 5) will reduce this swing of partial pressure and thereby cause a larger quantity of adsorbent to be used for the separation of the normals from the non-normals. During the desorption step, normal paraffin will load onto the top of an adsorbent bed in equilibrium with their concentration in the re-cycle gas. During a subsequent absorption step, this residual concentration of normals sets the limit as to how low the feed normals concentration can be reduced. Because of this the adsorption effluent (Str. 3 FIG. 5) leaving the top of a vessel during an adsorption (A-2) step, will always have a normal paraffin concentration higher than that of the recycle hydrogen. Valve leakage and normals front leakage will also contribute some impurities to the adsorption effluent. They represent about 50% of design impurities in this case. Therefore, it can be understood that to maintain a high adsorption effluent purity (or ultimately non-normals product purity), the normal paraffin content of the recycle hydrogen must be maintained at a low level.

The conventional way to maintain a low level of normals in the recycle hydrogen is to chill the isomerization reactor effluent (Str. 1, FIG. 5) to 60° F. The resulting normal paraffin content of the recycle hydrogen and the $C_5+$ non-normals products, after chilling to 60° F., can be seen in columns 1 and 2 of Table C.

By reducing the severity of cooling during product recovery from 60° F. to 85° F., the refrigeration package associated with conventional TIP units can be eliminated, thus saving the investment and the operating utilities of the chilling package. There are, however, penalties for doing this which will offset the above savings. As can be seen in columns 2 and 3 of Table C, the $nC_5+nC_6$ content of the recycle hydrogen has increased, relative to the 60° F. case, from 1.0 to 1.5 mole percent and the normals content of the $C_5+$ product has increased from 2.4 to 3.4 mole percent. The higher normals concentration is recycle hydrogen will also cause the normal paraffin delta loading in the adsorbers to drop, thereby requiring about 10 percent more adsorbent. This adsorbent increase will in turn also require a higher recycle hydrogen rate by about 10 percent. In addition to the above penalities, the quality of the product has dropped, as can be seen by a decrease in the produce RON-O, from 88.5 to 88.1.

Figure 6:
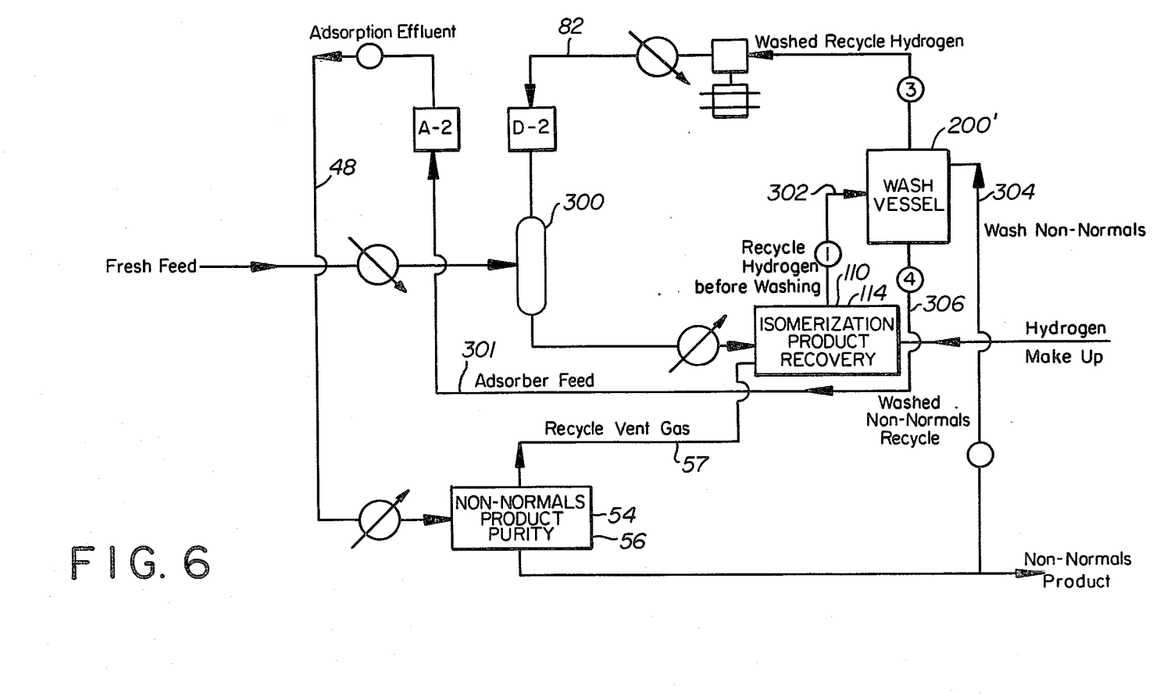

The penalties for increasing the product recovery temperature from 60° F. to 85° F. can be reduced by using non-normals product washing in accordance with the present invention as illustrated in FIG. 5. FIG. 6 depicts the TIP unit using non-normals product washing, in accordance with the present invention, to improve the recovery of normals from the recycle gas. In the arrangement of FIG. 6, the recycle hydrogen leaving the isomerization product recovery section enters the bottom of a trayed or packed column. In the column it is counter-currently washed with about 11 percent of the non-normals product. The recycle wash non-normals, which contain the normals removed from he recycle hydrogen, are recycled back to the adsorber feed to be re-processed in the adsorption section. The washed recycle hydrogen leaves from the top of the vessel to be recycled back to the adsorption section. Table D shows a material balance for the non-normals product washing which also used 85° F. cooling in the product recovery section of the unit. This material balance was simulated using 5 theoretical stages in the wash column.

It can be seen from the washed recycle hydrogen composition and the $C_5+$ non-normals product composition (Str. 5 and 6) in Table C, that the efficiency of the washing step in accordance with the present invention approaches that of chilling (to 60° F.) in the product recovery section. Non-normals washing of the recycle hydrogen has reduced the normals content of both the recycle hydrogen and the non-normals product back to the low level experienced before by the use of a chiller. The recycled wash non-normals stream will cause an increase in the adsorbent inventory and recycle hydrogen requirement of about 10 percent, and will also lead to proportionally higher fuel cost. Because of this, the wash non-normals rate will have to be carefully optimized during a design. However, due to the elimination of the refrigeration package the overall investment cost of the unit, relative to the conventional scheme, would be reduced by about 6 percent and the utilities due to compression equipment would be reduced by about 30 percent.

TABLE A

| | Material Balance for Normals Product Recovery in FIG. 2 (Prior Art) | | | | |
|---|---|---|---|---|---|
| | 1 | 2 | 3 | 4 | 5 |
| Stream No. | Vent Gas (mole/hr) | Desorption Effluent (mole/hr) | Hydrogen Make up (mole/hr) | Recycle Hydrogen (mole/hr) | Normals Product (mole/hr) |
| $H_2$ | 79.55 | 1261.34 | 1.21 | 1341.72 | 0.38 |
| $C_1$ | 1.53 | 25.67 | 0.16 | 27.30 | 0.06 |
| $C_2$ | 0.14 | 2.82 | 0.10 | 3.01 | 0.05 |
| $C_3$ | 0.14 | 1.55 | 0.06 | 1.64 | 0.11 |
| $nC_4$ | 0.09 | 2.68 | 0.01 | 2.22 | 0.56 |
| $iC_4$ | 0.20 | 0.85 | 0.01 | 0.90 | 0.16 |

TABLE A-continued

Material Balance for Normals Product Recovery in FIG. 2 (Prior Art)

| Stream No. | 1 Vent Gas (mole/hr) | 2 Desorption Effluent (mole/hr) | 3 Hydrogen Make up (mole/hr) | 4 Recycle Hydrogen (mole/hr) | 5 Normals Product (mole/hr) |
|---|---|---|---|---|---|
| $nC_5$ | 0.01 | 0.85 | — | 0.45 | 0.41 |
| $iC_5$ | 0.06 | 0.14 | 0.01 | 0.14 | 0.07 |
| $nC_6$ | 0.04 | 111.84 | — | 21.38 | 90.50 |
| $C_6$ isomers | 1.49 | 2.12 | 0.01 | 1.12 | 2.50 |
| $nC_7$ | — | 0.14 | — | 0.03 | 0.11 |
| $C_7$ isomers | 0.09 | 0.42 | — | 0.09 | 0.42 |
| | 83.34 | 1410.42 | 1.57 | 1400.00 | 95.33 |
| | | | | | 96.3 mole % |

$nC_6$ in Total $C_5+$ product

TABLE B

Material Balance for Normals Product Recovery using Normals Product Washing in FIG. 3 (Present invention)

| Stream No. | 1 Recycle Vent Gas Before Wash (mole/hr) | 2 Wash Normals (mole/hr) | 3 Recycle Wash Normals (mole/hr) | 4 Washed Recycle Vent Gas (mole/hr) | 5 Desorption Effluent (mole/hr) | 6 Hydrogen Make up (mole/hr) | 7 Recycle Hydrogen (mole/hr) | 8 Normal Product (mole/hr) |
|---|---|---|---|---|---|---|---|---|
| $H_2$ | 79.56 | 0.02 | 0.02 | 79.56 | 1261.48 | 1.21 | 1341.85 | 0.38 |
| $C_1$ | 1.54 | — | — | 1.54 | 25.80 | 0.16 | 27.43 | 0.07 |
| $C_2$ | 0.14 | — | — | 0.14 | 2.85 | 0.10 | 3.05 | 0 04 |
| $C_3$ | 0.15 | 0.01 | 0.01 | 0.15 | 1.60 | 0.06 | 1.70 | 0.10 |
| $nC_4$ | 0.09 | 0.04 | 0.03 | 0.10 | 2.80 | 0.01 | 2.32 | 0.55 |
| $iC_4$ | 0.20 | 0.01 | 0.03 | 0.18 | 0.82 | 0.01 | 0.86 | 0.14 |
| $nC_5$ | — | 0.03 | 0.02 | 0.01 | 0.84 | — | 0.42 | 0.40 |
| $iC_5$ | 0.06 | — | 0.03 | 0.03 | 0.08 | 0.01 | 0.08 | 0.04 |
| $nC_6$ | 0.05 | 4.94 | 3.93 | 1.06 | 115.86 | — | 21.77 | 90.27 |
| $C_6$ isomers | 1.50 | 0.09 | 1.15 | 0.44 | 1.53 | 0.01 | 0.54 | 1.35 |
| $nC_7$ | — | — | — | — | 0.11 | — | 0.01 | 0.10 |
| $C_7$ isomers | 0.09 | 0.02 | 0.09 | 0.02 | 0.36 | — | 0.03 | 0.33 |
| | 83.38 | 5.16 | 5.31 | 83.23 | 1413.13 | 1.57 | 1400.00 | 93.77 |
| | | | | | | | | 97.6 mole % |

$nC_6$ in Total $C_5+$ product

TABLE C (PRIOR ART)

Recycle Hydrogen Composition and $C_5+$ Product Composition for 85° F. Product Cooling Plus non-normals Product Washing and Product Cooling Only at 85 and 60° F.

| | 85° F. Product Cooling plus Non-normal Product Washing | | 85° F. Product Cooling without Non-normals Product Washing | | 60° F. Product Cooling without Non-normals Product Washing | |
|---|---|---|---|---|---|---|
| Stream No. | 1 Recycle Hydrogen (mole %) | 2 $C_5+$ Product (mole %) | 3 Recycle Hydrogen (mole %) | 4 $C_5+$ Product (mole %) | 5 Recycle Hydrogen (mole %) | 6 $C_5+$ Product (mole %) |
| $H_2$ | 70.0 | — | 65.7 | — | 65.5 | — |
| $C_1$ | 18.4 | — | 18.6 | — | 18.5 | — |
| $C_2$ | 5.5 | — | 6.5 | — | 6.7 | — |
| $C_3$ | 1.8 | — | 2.4 | — | 2.7 | — |
| $iC_4$ | 0.8 | — | 1.2 | — | 1.3 | — |
| $nC_4$ | 0.6 | — | 0.7 | — | 0.8 | — |
| $iC_5$ | 1.5 | 51.2 | 2.4 | 50.4 | 2.6 | 51.3 |
| $nC_5$ | 0.9 | 2.1 | 1.4 | 3.0 | 0.9 | 2.1 |
| CP | 0.1 | 2.7 | 0.1 | 2.6 | 0.1 | 2.6 |
| 2,2-DMB | 0.1 | 7.3 | 0.2 | 7.2 | 0.2 | 7.3 |
| 2,3-DMB | 0.1 | 4.1 | 0.1 | 4.1 | 0.1 | 4.2 |
| 2 MP | 0.2 | 16.0 | 0.3 | 16.0 | 0.3 | 16.1 |
| 3 MP | 0.1 | 10.3 | 0.2 | 10.4 | 0.2 | 10.4 |
| $nC_6$ | 0.1 | 0.3 | 0.1 | 0.4 | 0.1 | 0.2 |
| MCP | 0.1 | 4.4 | 0.1 | 4.4 | 0.1 | 4.3 |
| CH | 0.1 | 1.6 | 0.1 | 1.5 | 0.1 | 1.5 |
| | 100.0 | 100.0 | 100.0 | 100.0 | 100.0 | 100.0 |
| $nC_5 + nC_6$ Conc. | 1.0 | 2.4 | 1.5 | 3.4 | 0.9 | 2.3 |
| $C_5+$ Ron-O | | 88.5 | | 88.1 | | 88.5 |

TABLE D (PRESENT INVENTION)
Material Balance for Purifying Recycle Hydrogen using
Non-normal Product Washing in FIG. IV

| Stream No. | 1<br>Recycle Hydrogen<br>Before Non-normals<br>Wash<br>(mole/hr) | 2<br>Wash<br>Non-normals<br>(mole/hr) | 3<br>Washed<br>Recycle Hydrogen<br>(mole/hr) | 4<br>Recycle wash<br>Non-normals<br>(mole/hr) |
|---|---|---|---|---|
| $H_2$ | 12659.6 | 3.2 | 12659.7 | 3.1 |
| $C_1$ | 3583.6 | 6.9 | 3584.3 | 6.0 |
| $C_2$ | 1283.7 | 13.8 | 1286.6 | 10.9 |
| $C_3$ | 512.8 | 18.7 | 516.8 | 14.7 |
| $iC_4$ | 243.7 | 24.2 | 251.0 | 16.9 |
| $nC_4$ | 164.1 | 11.1 | 159.8 | 15.4 |
| $iC_5$ | 449.9 | 152.2 | 501.9 | 100.2 |
| $nC_5$ | 245.7 | 6.4 | 181.3 | 70.8 |
| CP | 12.9 | 7.8 | 15.7 | 5.0 |
| 2,2-DMB | 30.2 | 21.6 | 37.9 | 13.9 |
| 2,3-DMB | 13.2 | 12.3 | 17.4 | 8.1 |
| 2 MP | 49.4 | 47.8 | 63.2 | 34.0 |
| 3 MP | 33.0 | 30.8 | 39.5 | 24.3 |
| $nC_6$ | 27.1 | 0.5 | 6.6 | 21.0 |
| MCP | 9.7 | 12.9 | 13.8 | 8.8 |
| CH | 3.1 | 4.5 | 4.5 | 3.1 |
| | 19321.5 | 374.7 | 19340.0 | 356.2 |

What is claimed is:

1. In a process for separating normal paraffins and non-normal paraffins from a vapor state mixture containing the same wherein
   (i) said mixture is passed through in sequence a plurality of fixed beds an adsorbent system containing a zeolitic molecular sieve adsorbent which selectively adsorbs normal paraffins,
   (ii) a non-sorbable purge gas is used to (a) desorb normals from each bed to provide an effluent containing desorbed normals in mixture with purge gas and (b) transfer non adsorbed non-normal paraffins from each bed to provide a separate effluent containing non-normal paraffins in mixture with purge gas
   (iii) the effluent of (ii) (a) is separated into a purge gas stream containing residuals of normals and a normal product stream and said purge gas stream recycled and
   (iv) the effluent of (ii) (b) is separated into a purge gas stream containing residual non-normals and a non-normal product stream and said purge gas is recycled, the improvement for lowering the residual content of either the normals of non-normals of recycle purge gas which comprises washing the purge gas from a selected effluent of either (ii) (a) or (ii) (b) prior to recycle to the adsorbent system with a portion of the product stream from the non-selected effluent, the effluent of (ii) (a) being selected for the lowering of normals content and the effluent of (ii) (b) being selected for the lowering of non-normals content.

* * * * *